US00PP18673P3

(12) United States Plant Patent
Yencho et al.

(10) Patent No.: US PP18,673 P3
(45) Date of Patent: Apr. 1, 2008

(54) ORNAMENTAL SWEETPOTATO PLANT NAMED 'SWEET CAROLINE GREEN YELLOW'

(50) Latin Name: *Ipomoea batatas*
Varietal Denomination: Sweet Caroline Green Yellow

(75) Inventors: George Craig Yencho, Raleigh, NC (US); Kenneth Pecota, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 11/395,059

(22) Filed: Mar. 31, 2006

(65) Prior Publication Data

US 2007/0143895 P1 Jun. 21, 2007

Related U.S. Application Data

(60) Provisional application No. 60/752,486, filed on Dec. 21, 2005.

(51) Int. Cl.
*A01H 5/00* (2006.01)

(52) U.S. Cl. ..... Plt./258

(58) Field of Classification Search ..... Plt./258
See application file for complete search history.

*Primary Examiner*—Wendy C. Haas
*Assistant Examiner*—Georgia Helmer
(74) *Attorney, Agent, or Firm*—Myers Bigel Sibley & Sajovec P.A.

(57) ABSTRACT

*Ipomoea batatas* 'Sweet Caroline Green Yellow' is a moderately compact to slightly trailing cultivar. This cultivar is distinguishable from other cultivars by its green and yellow to light yellow variegation. The plant has moderate vigor, is moderately to well branched and is well suited for container production. The production of flowers by 'Sweet Caroline Green Yellow' is sparse to moderate under short day conditions.

2 Drawing Sheets

Latin name of the genus and species: The Latin name of the novel, ornamental plant variety disclosed herein is *Ipomoea batatas* (L.) Lam.

Variety denomination: The inventive cultivar of *Ipomoea batatas* disclosed herein has been given the varietal denomination 'Sweet Caroline Green Yellow'.

BACKGROUND OF THE INVENTION

*Ipomoea* species are members of the morning glory family Convolvulaceae. *Ipomoea batatas,* the cultivated species, is commonly produced for consumption and referred to as the white or yellow sweetpotato and the orange yarn. The plants are typically fast growing, green vines possessing a wide variety of leaf shapes ranging from palmate and deeply lobed, to cordate or triangular shaped leaves with no lobes. Ornamental sweetpotatoes, which have been bred and selected for their unique foliage colors, leaf shapes and plant habits, typically do not produce large fleshy storage roots like the sweetpotato cultivated for consumption. In comparison, storage roots produced by ornamental sweetpotatoes are typically not as large because no selection has been exercised for yield, thus storage roots do not begin to swell until very late in the season. Further, the few storage roots that are formed by ornamental sweetpotatoes are typically not as attractive as those produced by the table-stock types as they are generally cracked, very malformed, often mottled in skin and flesh color, and are not palatable.

Late in the growing season when day-lengths begin to shorten or when the plants are stressed, ornamental sweetpotato plants produce tubular flowers that are similar to morning glories, but most plantings are dominated by the appearance of the foliage. The plants are highly desirable due to their ability to grow under varied stress conditions, cover a large space, and last the entire growing season. Moreover, these plants have few insect or disease problems.

Until the release of the Sweet Caroline series of ornamental sweet potatoes (see below) there were six popular types of *Ipomoea batatas* ornamental sweetpotatoes being cultivated primarily for their annual, summer vines in landscaping applications. These six cultivars are: 'Blackie' (not patented), having purple foliage and lavender flowers; 'Terrace Lime' (not patented) and 'Margarita' (not patented; also known as 'Sulfur'), which have large brilliant chartreuse leaves and lavender blooms; 'Black Heart' (not patented; also known as 'Ace of Spades'), having heart-shaped leaves with burgundy purple color; 'Tricolor' (not patented; also known as 'Pink Frost'), a variegated plant having pale green, white, and pink-margined leaves; and 'Lady Fingers' (unpatented), which has medium green, dainty leaves divided into long, thin, fingerlike lobes that are complemented by burgundy stems and veins.

*Ipomoea batatas* 'Margarita' was recently released in the United States, and has become widely used as a landscape annual. However, it is not suitable for mixed containers as this variety exhibits a very vigorous growth and tends to out-compete other species. See Armitage. A. M. and J. M. Garner, (2001) *Ipomoea batatas* 'Margarita'. HortScience 36:178. Another popular variety, 'Blackie', is a vigorous purple-leaved clone, which is also unsuited to containerized gardens.

Therefore, to meet the current horticultural demand, it is desirable to produce new, more robust cultivars of ornamental sweetpotato with attractive foliage colors, leaf shapes, and plant architectures. In addition, it would be advantageous to develop cultivars of ornamental sweetpotato exhibiting a more compact growth, and which do not out-compete other species in mixed containers.

*Ipomoea batatas* 'Sweet Caroline Light Green' (U.S. Pat. No. PP15,028, issued Jul. 20, 2004), 'Sweet Caroline Green' (U.S. Pat. No. PP15,056, issued Aug. 3, 2004), 'Sweet Caroline Bronze' (U.S. Pat. No. PP15,437, issued Dec. 21, 2004), 'Sweet Caroline Purple' (U.S. Pat. No. PP14,912, issued Jun. 15, 2004), and 'Sweet Caroline Red' (U.S. Pat. No. PP17,483, issued Mar. 13, 2007) are recently introduced cultivars developed at North Caroline State University that are characterized by compact growth habit, moderate to deeply lobed palmate leaves, and attractive foliage color.

The present invention relates to a new and distinct variety of *Ipomoea batatas* named 'Sweet Caroline Green Yellow'. This variety is a moderately compact to slightly trailing variety, and it is distinguishable from other varieties by its green foliage with yellow to light yellow variegation, which is not currently available in ornamental sweetpotatoes. The plant has moderate vigor, is moderately to well branched, and is well suited for container production.

Lineage. The *Ipomoea batatas* 'Sweet Caroline Green Yellow' cultivar (breeding designation NC2626-2ORN) is derived from seed of open pollinated 'Okinawa' (not patented) collected in Kona, Hi., during November 2002. As a result of being derived from seed resulting from open pollination, the male parent is unknown. The harvested seed was brought to North Carolina State University and assigned the family name NC2626 in the winter of 2003. The family NC2626 contained a total of 68 open pollinated seed. All of these seed were planted in Raleigh, N.C., during Spring 2003. The single, individual plant now known as *Ipomoea batatas* 'Sweet Caroline Green Yellow' was selected in August/September 2003 because of its combination of exceptional features, including its variegation, and has been propagated asexually since that time.

Asexual Reproduction. Since its selection, *Ipomoea batatas* 'Sweet Caroline Green Yellow' has been asexually reproduced at Raleigh, N.C., predominantly by vegetative propagation of vine cuttings. Successively, there have been three cycles of vegetative propagation, one cycle of tissue culture micropropagation, and multiple vegetative propagation cycles to increase the plant population. Asexual reproduction of the new Ornamental Sweetpotato cultivar by cuttings has shown that the unique features of the new cultivar are stable and the plant reproduces true to type in successive generations of asexual reproduction.

SUMMARY OF THE INVENTION

*Ipomoea batatas* 'Sweet Caroline Green Yellow' is a moderately compact to slightly trailing cultivar. This cultivar is distinguishable from other cultivars by its green and yellow to light yellow variegation. The plant has moderate vigor, is moderately to well branched and is well suited for container production. The production of flowers by 'Sweet Caroline Green Yellow' is sparse to moderate under short day conditions.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which accurately describe the colors of the new *Ipomoea batatas*.

DETAILED BOTANICAL DESCRIPTION

The following is a detailed description of the botanical characteristics of the new and distinct cultivar of *Ipomoea batatas* plant known by the denomination 'Sweet Caroline Green Yellow'. All colors cited herein refer to The Royal Horticultural Society Colour Chart (The Royal Horticultural Society, London, 1995 edition) designations except where general terms of ordinary dictionary significance are used. Where dimensions, sizes, colors, and other characteristics are given, it is to be understood that such characteristics are approximations or averages set forth as accurately as practicable.

The descriptions reported herein are from 11-week-old specimens. *Ipomoea batatas,* 'Sweet Caroline Green Yellow' has not been observed under all possible environmental conditions; therefore, the phenotype may vary under different environmental conditions such as season, temperature, light intensity, day length, cultural conditions, and the like, without however any variance in the genotype.

Technical Description of the Variety.

Above-Ground structure. Overall, the cultivar, *Ipomoea batatas* 'Sweet Caroline Green Yellow', is a moderately compact to slightly trailing herbaceous plant. Plant height is 22 cm and area of spread is 30×38 cm. It is a moderately fast growth with moderate vigor. Foliage is dense due to many leaves, and results in a round uniform plant habit, although more vining than that of *Ipomoea batatas,* 'Sweet Caroline Sweetheart Light Green' (U.S. Plant application Publication 20070143896 dated Jun. 21, 2007).

Branching habitat. Very free branching with no basal shoots.

Lateral shoots. The number of lateral shoots varies, but averages around 6, with multiple short secondary shoots. Lateral branch length about ~38 cm. Diameter: 0.4 cm. Internodes have an average length of 2 cm. Stems are round, smooth and sturdy, without any pubescence. Shoots are initially upright but then fall outward, forming a dense canopy. Color: bright yellow green (RHS 145A).

Petiole. Average length: 6.6 cm. Diameter: 0.25 cm. Texture: smooth. Color: 146C above and below.

Figure 1:
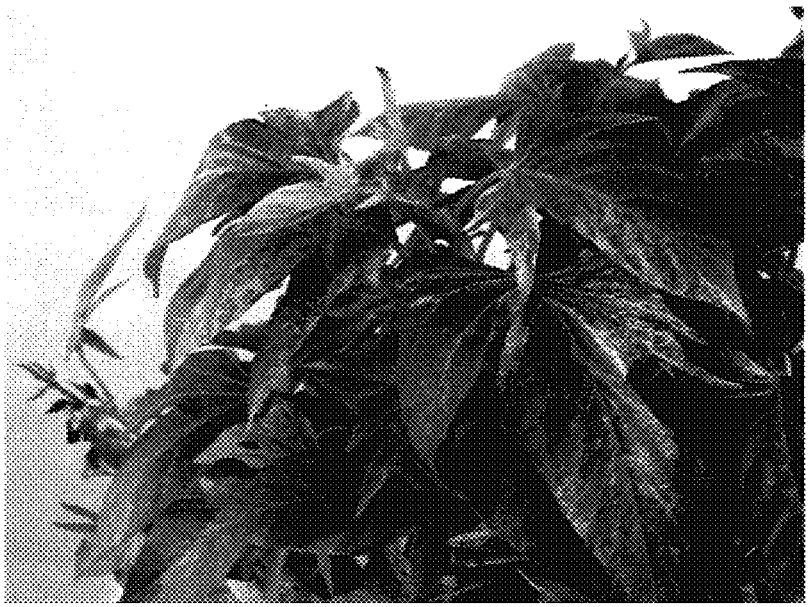
FIG. 1 is a color photograph showing both new and mature foliage produced by *Ipomoea batatas* 'Sweet Caroline Green Yellow'. The plant shown in FIG. 1 is 11 weeks of age.
Figure 2:
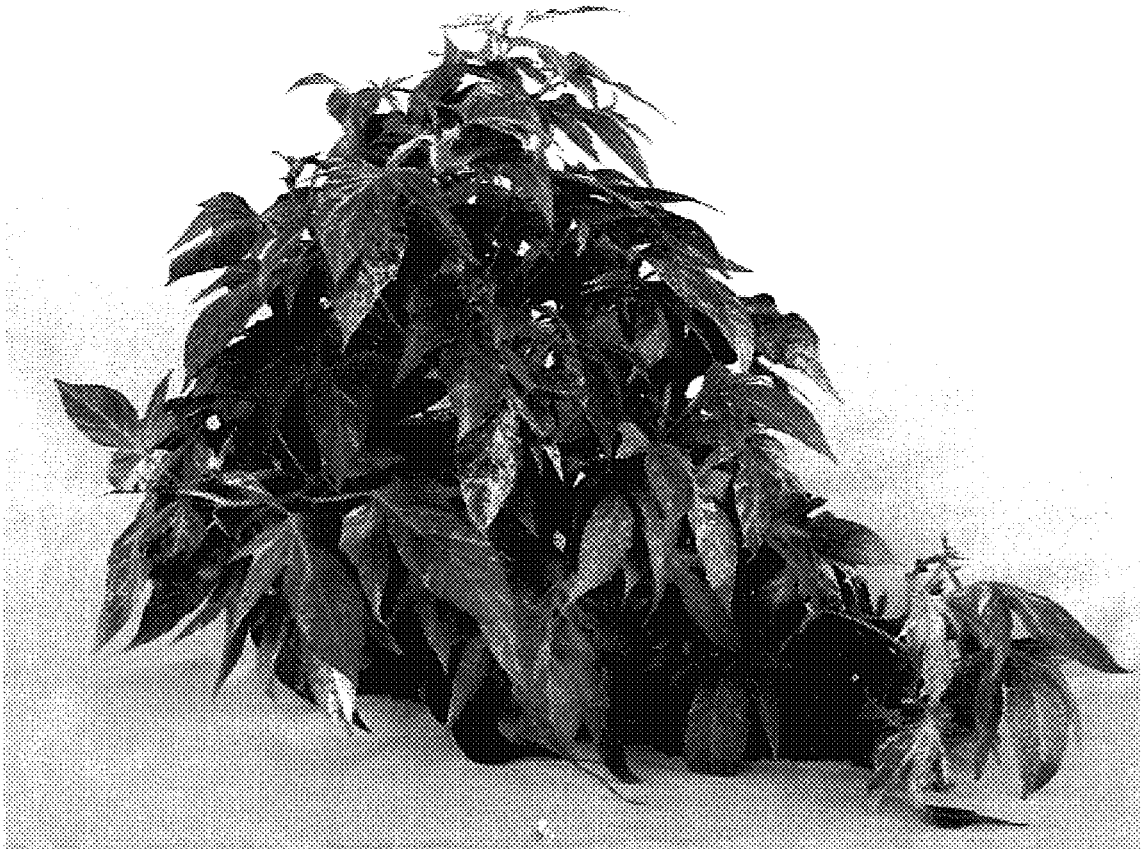
FIG. 2 is a color photograph showing a typical plant of the variety *Ipomoea batatas* 'Sweet Caroline Green Yellow'. The plant shown in FIG. 2 is 11 weeks of age.

Foliage. Leaves are alternate and tend to spiral around the stems. They are simple but five-pointed, almost maple-like but with longer and wider center lobe and 2 smaller points on either side (FIGS. 1 and 2). The number of leaves per stem varies with stem length but an average stem has about ~20 leaves. Leaf tip is acuminate and base is truncate. Leaf margins are entire but five-pointed. Leaves are smooth and mat with no pubescence. Leaf length averages 8 cm. Leaf width averages 8.5 cm. Venation: palmate at the base, becoming arcuate toward the leaf tip. Foliage is very dense and the variegated five-pointed leaves are very decorative. Color: see Table 1.

TABLE 1

| Leaf Structure | Upper Surface | Lower Surface |
|---|---|---|
| Young Leaf | Bright green, RHS 144A | Bright green, RHS 144A |
| Mature Leaf | Green, RHS 147A, with irregular flecks and streaks of 145B and 146C. | Green, RHS 147B, with flecks of 145C |
| Vein | 146B | 146B |

Flowers. The production of flowers by 'Sweet Caroline Green Yellow' is rare to sparse under short day conditions. The precise photoperiod for flower induction is currently unknown. Flowering may also occur sporadically throughout the season in response to a variety of stressful conditions (e.g., drought, nutrient stress, cloudy weather). It is noted that not only is flowering in their variety rare, but also, when flowers are produced, they are ephemeral (in most cases open only in the morning).

The inflorescence is generally a cyme in which the peduncle is divided into multiple axillary peduncles. Peduncles are green (Color: 144C), averaging 41 mm long from mature leaf axils with an average diameter of 2 mm. Usually buds of the first, second, and third order are developed, but sometimes, single flowers are produced. Buds are yellow colored (Color: 150B to 150C), ovate, and around 21 mm in length and 5 mm in diameter 24 hours before opening.

The corolla is composed of five fused petals that form a funnel with a pentagonal limb. Corolla width: about ~3.9 cm, corolla length: about ~3.7 cm. The corolla is not fragrant. The limb color is light lavender, while the outer throat color is lavender and the inner throat color is purple. Inner limb color: 76D, Outer limb color: 76D, Inner throat color: 77A, Outer throat color: 76D. There are five sepals, with an average length of 8.6 mm and width of 3.5 mm. The sepals are obovate with a caudate apex and green in color. Outer sepal color: 146B, Inner sepal color: 146C.

Each flower has one pistil with a white colored style (Color: 155B). The stigma is cream colored (Color: 157B) and averages about 2 mm wide and 18 mm long and has two segments. The stigma is exerted relative to the stamens. The ovary is yellow (Color: 1C) and superior with two locules that contain one or two ovules. Orange basal glands (Color: 17A) containing nectar continuing halfway up the ovary are at the base of the ovary. There are five cream colored anthers (Color: 158C) that are approximately 3 mm long. Pollen (158C) is abundant. True seed are difficult to obtain, even with compatible crosses. There is some variation in flower size and color, depending on the environmental conditions. Descriptions are based on: CIP, AVRDC, IBPGR, 1991. Descriptors for Sweet Potato, Huaman, Z., editor. International board for Plant Genetic Resources, Rome, Italy.

Figure 3:
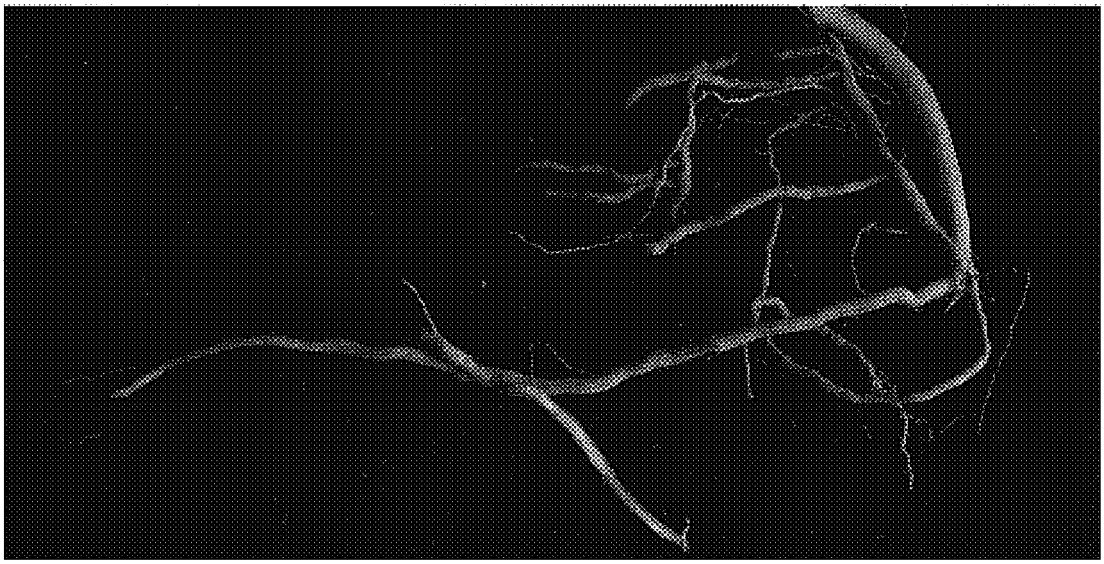
FIG. 3 is a color photograph showing typical storage roots produced by *Ipomoea batatas,* 'Sweet Caroline Green Yellow' 123 days after planting. Plants were planted as five-hill plots spaced 30.5 cm apart in the row at the Horticultural Crops Research Station, Clinton, N.C. USA.

Below-Ground structure. Plants form no, to very small, underground storage roots that are highly malformed and do not meet USDA Sweetpotato Storage Root Grade Standards (FIG. 3). Storage roots that do form typically possess cream colored skin (159A) with a thin light purple layer immediately beneath the skin (N79C) and cream colored flesh (158A).

Growth conditions. *Ipomoea batatas* 'Sweet Caroline Green Yellow' had moderate vigor and a moderate growth rate. It is very adaptable to container culture. In locales with mild winter conditions, *Ipomoea batatas,* 'Sweet Caroline Green Yellow' will grow perennially; otherwise it is an annual plant. Similar to cultivated sweetpotatoes, wind or rain rarely causes much damage to 'Sweet Caroline Green Yellow', but if damage does occur, the plant drops the damaged leaves and grows new shoots at nodes where the leaves were lost.

Disease or pest resistance. *Ipomoea batatas* 'Sweet Caroline Green Yellow' is susceptible to Sweetpotato Feathery Mottle Virus and damage by Japanese beetles. A low to moderate amount of sun-induced leaf burning has been observed in 'Sweet Caroline Green Yellow' when plants are young or under excessive moisture stress. The burning typically occurs in the yellow areas of the leaves leaving the green areas undamaged. As the plants grow in size this damage becomes less problematic.

Comparison with Other *Ipomoea batatas* Cultivars.

'Sweet Caroline Green Yellow' is very distinct based on variegation and relative vigor. (Table 2). Of the most common cultivars of ornamental sweetpotato, *Ipomoea batatas* 'Sweet Caroline Green Yellow' is best compared with 'Tricolor' (unpatented; also known as 'Pink Frost'), also a variegated plant which has pale green and white leaves with pink highlighting. Like 'Tricolor', 'Sweet Caroline Green Yellow' has variegated foliage but the variegation is green and yellow. Further, 'Sweet Caroline Green Yellow' grows more vigorously than 'Tricolor' and its leaves are larger and their shape less distorted.

'Sweet Caroline Green Yellow' was obtained from open pollinated seed of the cultivar 'Okinawa' (female parent; not patented); therefore the male parent is unknown. 'Okinawa', a tablestock-type sweetpotato, produces a very vigorous, highly trailing, green vine and has solid green leaves that are moderately to deeply lobed.

TABLE 2

| Characteristic | New Variety 'Sweet Caroline Green Yellow' | Comparison 1 'Tricolor' |
|---|---|---|
| Plant Habit | Moderately Compact to Slightly Trailing | Compact |
| Foliage Color | Green and Light Yellow Variegated | Green, White and Pink Variegated |
| Leaf Size | Medium | Small |
| Leaf Shape | Moderate to Deeply Lobed | Moderate to Deeply Lobed |

What is claimed is:

1. A new and distinct cultivar of *Ipomoea batatas* plant named 'Sweet Caroline Green Yellow', substantially as illustrated and described herein.

* * * * *

UNITED STATES PATENT AND TRADEMARK OFFICE

CERTIFICATE OF CORRECTION

PATENT NO. : PP 18,673 P3
APPLICATION NO. : 11/395059
DATED : April 1, 2008
INVENTOR(S) : Yencho et al.

It is certified that error appears in the above-identified patent and that said Letters Patent is hereby corrected as shown below:

Column 5, The paragraph beginning with "Flowers", line 7:
Please correct "It is noted that not only is flowering in their variety rare"
To read -- It is noted that not only is flowering in this variety rare --

Signed and Sealed this

First Day of July, 2008

JON W. DUDAS
*Director of the United States Patent and Trademark Office*